United States Patent [19]

Knoll

[11] Patent Number: 4,992,266

[45] Date of Patent: Feb. 12, 1991

[54] REDUCING THE OCULAR IRRITANCY OF ANIONIC SHAMPOOS

[75] Inventor: Donald W Knoll, Waukesha, Wis.

[73] Assignee: S. C. Johnson & Son, Inc., Racine, Wis.

[21] Appl. No.: 393,438

[22] Filed: Aug. 14, 1989

[51] Int. Cl.$^5$ .............. A61K 7/75; A61K 7/5; C11D 1/02; C11D 1/12

[52] U.S. Cl. .................... 424/70; 424/78; 252/174.21; 252/174.23; 252/550; 252/554; 252/558; 252/DIG. 13

[58] Field of Search ............... 424/70, 78; 252/550-559, DIG. 13, 174.21, 174.23

[56] References Cited

U.S. PATENT DOCUMENTS

| | | | |
|---|---|---|---|
| 2,309,722 | 2/1943 | Wilkes et al. | 424/70 |
| 2,991,229 | 7/1961 | Ivison | 424/49 |
| 2,999,068 | 5/1961 | Pilcher et al. | 252/528 |
| 3,001,944 | 9/1961 | Wei | 252/117 |
| 3,086,943 | 4/1963 | Lang | 252/546 |
| 3,095,381 | 6/1963 | Tinnon et al. | 252/550 |
| 3,598,746 | 8/1971 | Kaniecki et al. | 252/122 |
| 3,630,934 | 12/1971 | Kelly et al. | 252/547 |
| 3,634,271 | 1/1972 | Friedman et al. | 252/545 |
| 3,649,543 | 3/1972 | Cahn et al. | 252/526 |
| 3,763,047 | 10/1973 | Fairs | 252/99 |
| 3,767,788 | 10/1973 | Rankin | 424/78 |
| 3,783,872 | 1/1974 | King | 604/368 |
| 3,798,182 | 3/1974 | Kelly et al. | 252/546 |
| 3,811,349 | 5/1974 | Jennings | 83/14 |
| 3,813,350 | 5/1974 | Kelly et al. | 252/547 |
| 3,819,528 | 6/1974 | Berry | 252/153 |
| 3,856,919 | 12/1974 | Rankin | 424/78 |
| 3,868,445 | 2/1975 | Ryde et al. | 424/429 |
| 3,880,766 | 4/1975 | Kalopissis et al. | 252/173 |
| 3,882,036 | 5/1975 | Krezanoski et al. | 252/106 |
| 3,882,038 | 5/1975 | Clayton et al. | 252/164 |
| 3,890,238 | 6/1975 | Boehmer | 252/1 |
| 3,896,040 | 7/1975 | Danesh | 252/174.21 |
| 3,928,251 | 12/1975 | Bolich et al. | 252/545 |
| 3,944,663 | 3/1976 | Weiss et al. | 424/78 |
| 3,947,573 | 3/1976 | Rankin | 424/80 |
| 4,148,743 | 4/1979 | Schubert | 252/132 |
| 4,154,706 | 5/1979 | Kenkare et al. | 225/547 |
| 4,169,067 | 9/1979 | Joshi | 252/132 |
| 4,310,434 | 1/1982 | Choy et al. | 252/174.21 |
| 4,336,151 | 6/1982 | Like et al. | 252/174.21 X |
| 4,398,045 | 8/1983 | Sebag | 568/624 |
| 4,450,091 | 5/1984 | Schmolka | 252/174.21 |
| 4,451,385 | 5/1984 | Tavss et al. | 252/132 |
| 4,544,495 | 1/1985 | Schmolka | 252/174.21 |
| 4,582,626 | 4/1986 | Ferrara | 252/122 |
| 4,780,249 | 10/1988 | Pittz et al. | 252/547 |

FOREIGN PATENT DOCUMENTS

WO88/05812 8/1988 World Int. Prop. O. .

OTHER PUBLICATIONS

"Reduction of Topical Irritation", Goldemberg et al., *J. Soc. Cosmet. Chem.*, vol. 28, pp. 667–679 (Nov. 1977).

"Relationship Between the Primary Dermal Irritation Index and Ocular Irritation", Gilman et al., *J. Toxicol.-Cut. & Ocular Toxicol* 2 (2&3), pp. 107–117 (1983).

"Detergent Toxicity Survey", Seabaugh et al., *Am. J. Pub. Health*, 67(4), pp. 367–369 (1977).

"Foam Enhancement and Eye Irritation Mitigation Properties of PLURONIC(R) Surfactants", BASF Corporation Chemicals Division, 15 pages, Mar. 17, 1986.

*Encyclopedia of Shampoo Ingredients*, Hunting, Micelle Press, Inc., Cranford, N.J. (1983), Formulas S065, S067, S075, S344, S365, S372, S383, S390, S424, S112, S124, S150, S220, S222, S155, and S289 located among pp. 31–122 and 308–310.

"Polyox(R) Water-Soluble Resins are Unique", Brochure No. F-44029C 3/81-5M, Union Carbide Corp., Danbury, Conn. (1981), 32 pages.

"Preparation and Properties of Low Irritation Shampoos", I. R. Schmolka, received from BASF Wyandotte Corp. on 08/03/82, 26 pages.

*Primary Examiner*—Thurman K. Page
*Assistant Examiner*—Suzan S. Rucker

[57] ABSTRACT

The ocular irritancy of aqueous shampoo compositions containing from about 1 to 20% by weight of an eye irritating anionic surfactant such as a $C_8$–$C_{18}$ alkyl sulfate containing from 0 to about 4 ethyleneoxy units is reduced by the addition of from about 0.01% to 5% of an ethylene oxide homopolymer. The homopolymer has the formula $H(OCH_2CH_2)_xOH$ where x has a value such that the weight average molecular weight of the homopolymer is between about 100,000 and 5,000,000, preferably between about 500,000 and 4,000,000. The resulting compositions are useful as hair shampoos as well as for cleaning the face and body.

7 Claims, No Drawings

REDUCING THE OCULAR IRRITANCY OF ANIONIC SHAMPOOS

TECHNICAL FIELD

This invention relates to a method of reducing the ocular irritancy of an aqueous shampoo composition containing certain eye irritating anionic surfactants through the use of a relatively small amount of a high molecular weight homopolymer of ethylene oxide.

BACKGROUND ART

Anionic surfactants containing sulfate or sulfonate functional groups have been used in shampoo formulations for a number of years because of their excellent ability to clean the hair. One disadvantage of the use of such surfactants is that they tend to irritate the eyes. In the *Journal of the Society of Cosmetic Chemists*, Vol. 28, pages 667-679 (Nov., 1977), entitled: "Reduction of topical irritation," Goldemberg et al. note that various compounds such as amphoteric surfactants like fatty alkyl betaine surfactants have been combined with surfactants such as lauryl sulfates to reduce the ocular irritancy of the harsh lauryl sulfate surfactants. Various other types of surfactants such as fatty alkyl alkanolamides have also been employed to reduce the ocular irritancy of sulfate surfactants. As a result, combinations of various surfactants have been employed to reduce the ocular irritancy of the major anionic surfactant present for the purpose of cleaning the hair.

U.S. Pat. No. 3,944,663 to Weiss et al. teaches mild light duty detergents containing homopolymers of ethylene oxide. Weiss et al. teaches that from about 0.01 to 5% by weight of a homopolymer of ethylene oxide of molecular weight between about $1 \times 10^5$ and $4 \times 10^6$ can be employed in detergent compositions including an anionic surfactant having skin irritating characteristics such as a $C_8$–$C_{18}$ alkyl benzene sulfonate or a $C_8$–$C_{18}$ alkyl sulfate containing from 0 to 3 ethyleneoxy units per molecule to reduce the skin irritation of the hands by a light duty liquid or powder detergent formulation containing from 10 to 35% by weight of such irritating anionic surfactants. Weiss et al. suggests nothing concerning the effect such high molecular weight ethylene oxide homopolymers might have upon the ocular irritancy of such anionic surfactants.

In a Journal article entitled "Relationship Between The Primary Dermal Irritation Index and Ocular Irritation," Gilman et al., *J. Toxicol.-Cut. & Ocular Toxicol.*, 2(2 and 3), 107-117 (1983), Gilman et al. provide data to show that high dermal irritation potential of compounds does not necessarily suggest that these compounds will also exhibit high ocular irritation. In this paper, Gilman et al. argue very strongly that due to the different histologies of the skin and eye, it is not necessarily obvious that a compound which exhibits a high dermal irritation potential will also exhibit high ocular irritancy. Gilman et al. note that a number of compounds which irritate the skin result in little to very low ocular irritation. Gilman et al. further note a paper by Seabaugh et al. entitled "Detergent toxicity survey", *Am. J. Pub. Health*, 67(4):367, 1977, as showing that certain products such as automatic dishwasher detergents and all purpose cleaners and laundry detergents could exhibit moderate to severe eye irritation and still possess negative dermal irritation indices. After reviewing the data, Gilman et al. conclude that one must test compounds for both dermal and ocular irritancy and one cannot simply assume that because dermal irritancy exists, ocular irritancy necessarily follows.

U.S. Pat. No. 3,767,788 to Rankin teaches an ophthalmic solution for use as a wetting agent for the eye that is an aqueous solution of from about 0.05 to about 2 weight percent of an ethylene oxide polymer having a molecular weight of at least 100,000 to act as an eye lubricant and a thickening agent. These polymers are said to have a low level of oral toxicity and an extreme level of compatibility in contact with the skin or in the eye. A humectant can also be included such as a polyalkylene glycol of molecular weight up to about 6,000. Furthermore, the solution can contain an ophthalmic medicament, particularly those requiring an acid pH, or a nonionic surfactant. This patent does not suggest using high molecular weight homopolymers of ethylene oxide to reduce the eye irritation of otherwise eye irritating anionic surfactants.

BASF Corporation Chemicals Division has reported that 3% of certain of their PLURONIC$^R$ Surfactants, which are block copolymers of polyethylene oxide and polypropylene oxide, were found to reduce the Draize eye irritancy scores of compositions containing 12% of anionic surfactants such as sodium laureth-3 sulfate. However, this fails to suggest that the same would be true for small amounts of ethylene oxide homopolymers.

SUMMARY DISCLOSURE OF INVENTION

It is one object of the present invention to provide a shampoo composition which exhibits reduced ocular irritation without a need for the further inclusion of an amphoteric or other ocular irritation reducing compound or surfactant such as a fatty alkyl betaine.

It is another object of the present invention to provide a method for reducing the ocular irritancy of a shampoo composition through the use of a minimum amount of a high molecular weight polymeric additive.

These and other objects and advantages of the present invention are provided by a method of reducing the ocular irritancy of a shampoo composition consisting essentially of at least one eye irritating anionic surfactant selected from the group consisting of $C_8$–$C_{18}$ alkyl sulfates containing from 0 to an average of about 4 ethyleneoxy units per molecule, $C_8$–$C_{18}$ alkyl benzene sulfonates, $C_8$–$C_{25}$ olefin sulfonates, $C_{10}$–$C_{20}$ paraffin sulfonates, $C_8$–$C_9$ alkyl phenol ethoxamer sulfates and mixtures thereof with the balance consisting essentially of water and other additives commonly included in shampoos such as thickeners, fragrances, dyes, proteins, and the like. The method comprises including within the shampoo composition, from about 0.005 to about 5%, more preferably from about 0.01 to 1% by weight, and most preferably from about 0.01 to 0.5% by weight of an ethylene oxide homopolymer of the formula $H(OCH_2CH_2)_xOH$ as the sole additive to reduce the ocular irritation of the shampoo, the value of x being such that the weight average molecular weight of the homopolymer is from about 100,000 to about 5,000,000. Preferably the molecular weight of the homopolymer is between 500,000 and 4,000,000 and, most preferably, the homopolymer has a weight average molecular weight of about 2,000,000. The compositions obtained by the method of this invention possess reduced ocular irritation when compared with the same formulations which do not contain such homopolymers. They are useful as shampoos for the hair.

BEST MODE FOR CARRYING OUT THE INVENTION

The shampoos obtained using the method of this invention are aqueous compositions containing from about 1 to about 20% by weight, more preferably, from about 5% to 15% by weight of at least one eye irritating anionic surfactant selected from the group consisting of $C_8$–$C_{18}$ alkyl sulfates containing from 0 to an average of about 4 ethyleneoxy units per molecule such as sodium lauryl sulfate, ammonium lauryl sulfate, alkyl sulfates of the general formula $R(OCH_2CH_2)_nOSO_3X$ where n has an average value of between 1 and 4, R is an alkyl group of from 8 to 18 carbon atoms such as octyl, lauryl, myristyl, and stearyl, and X is an anion such as sodium, potassium, ammonium, or an amine such as triethyl amine or triethanol amine. Other anionic surfactants which are known to have eye irritating properties can include linear alkyl benzene sulfonates having a $C_8$–$C_{18}$ alkyl chain such octyl, lauryl, myristyl, and stearyl. These can be employed in the form of sulfonates which are sodium or ammonium salts of such surfactants. An example of such a surfactant is sodium dodecyl benzene sulfonate. Other anionic surfactants can be $C_8$–$C_{25}$ olefin sulfonates such as $C_{14}$–$C_{16}$ olefin sulfonate and sodium $C_{16}$–$C_{18}$ olefin sulfonate; $C_{10}$–$C_{20}$ paraffin sulfonates, such as those having from about 10 to 20, preferably about 15–20 carbon atoms such as the primary paraffin sulfonates made by reacting long chain alpha olefins and bisulfites (e.g., sodium bisulfite) or paraffin sulfonates having the sulfonate groups distributed along the paraffin chain such as the products made by reacting a long chain paraffin with sulphur dioxide and oxygen under ultraviolet light followed by neutralization with sodium hydroxide or other suitable base; and $C_8$–$C_9$ alkyl phenyl ethoxamer sulfates such as sodium nonoxynol-1 sulfate, sodium nonoxynol-4 sulfate, sodium octoxynol-2 ethane sulfonate, and ammonium nonoxynol-4 sulfate.

Mixtures of one or more of the above anionic surfactants can be employed in the shampoo compositions. More preferably, the anionic surfactants are selected from $C_8$–$C_{18}$ alkyl sulfates containing from 0 to an average of about 4 ethyleneoxy units per molecule and more preferably, $C_{12}$ alkyl sulfates. A single alkyl sulfate or alkyl ether sulfate can be employed or a mixture of the same such as blend of a 50:50 weight ratio of ammonium lauryl sulfate and ammonium lauryl ether sulfate containing between 1 and 4 ethyleneoxy units per molecule can be employed. These surfactants are well known to those of ordinary skill in the art and many are available commercially.

For the purposes of this invention, the term "consisting essentially of" as used when referring to the shampoo composition means that the shampoo composition is free of surfactants such as fatty alkyl betaines and alkanolamides which have been employed in the past to reduce the ocular irritancy of the sulfate and sulfonate surfactants.

The method of the present invention employs from about 0.005 to about 5% of a high molecular weight polyethylene oxide polymer of the formula $H(OCH_2CH_2)_xOH$ as a sole additive to reduce the ocular irritation of the shampoo composition, the value of x being such that the weight average molecular weight of the homopolymer is from about 100,000 to about 5,000,000. More preferably, a higher molecular weight homopolymer is employed having a molecular weight of between 500,000 to about 4,000,000 and most preferably, the homopolymer has a molecular weight of about 2,000,000. These homopolymers are well known to those of ordinary skill in the art and are sold by Union Carbide Corporation under the registered trademark POLYOX.

The amount of homopolymer required to reduce the ocular irritancy of the anionic surfactants present inversely varies with the molecular weight of the ethylene oxide homopolymer. Thus it was found that about 0.01% of a homopolymer of ethylene oxide having a weight average molecular weight of about 2,000,000 was needed to significantly reduce the ocular irritation of an anionic surfactant containing shampoo composition as will be further described, infra. It is anticipated that higher amounts of the ethylene oxide homopolymer will be required for a given amount of anionic surfactant in a shampoo composition when lower molecular weight homopolymers are employed. Because of the effect that the homopolymer of ethylene oxide has on the viscosity of shampoo compositions, small amounts of high molecular weight ethylene oxide homopolymers are preferably employed. A use level of from 0.01% to no more than .5% and preferably, no more than about about 0.1%, is presently preferred as is a homopolymer of ethylene oxide having a weight average molecular weight of about 2,000,000.

Typically, shampoos based on anionic surfactants have a pH in the range of from about 3.0 to about 6.5. The pH of the compositions made by the present invention can be adjusted with organic or inorganic acids of the type commonly used in cosmetic compositions such as citric acid and phosphoric acid.

The remainder of the composition consists essentially of water, which is preferably in the form of deionized water.

The shampoo compositions contemplated as being useful in the present invention can further include other conventional additives in small amounts of no more than about 5%. Examples of such conventional additives are proteins, thickening agents, inorganic salts such as sodium chloride and ammonium chloride, dyes, fragrances, preservatives, conditioning agents which are compatible with the anionic surfactants present, and the like.

INDUSTRIAL APPLICABILITY

The method of the present invention is practiced by adding the water soluble ingredients such as the ethylene oxide homopolymer and surfactants together with the water to form a solution and separately mixing the oil soluble ingredients such as the pearlizing agents, conditioning agents, and moisturizing agents to form a second mixture which is then dispersed into the aqueous solution with agitation. After mixing well, the fragrance is then added. Alternatively, all of the ingredients except the volatile fragrance can be added to the water with agitation and the mixture can be heated to melt the ingredients being added, typically to about 48.89° C. (120° F.) and agitated until the mixture is homogeneous. The mixture is then cooled to room temperature (about 20°–25° C.) and the fragrance is added with agitation. Inline blending of ingredients can also be employed. The order of ingredient addition is not felt to be critical.

The improved compositions are useful as shampoos for the hair, although they can be used for cleaning the face and hands.

The following Examples are provided to show various aspects of the present invention without departing from the scope and spirit of the invention. Unless otherwise indicated, all parts and percentages used in the examples are by weight.

EXAMPLES 1-7

These Examples demonstrate the reduction in ocular irritancy of shampoo compositions containing fatty alkyl sulfate surfactants resulting from the addition of a small amount of an ethylene oxide homopolymer (Example 1) versus comparative examples containing no additives (Examples 2) or other conventional ocular irritancy reduction additives (Examples 3-7).

Each shampoo composition had the formulation given in Table I and the resulting pH and viscosity are also reported therein. The general procedure used to prepare Examples 1-7 was as follows: The surfactants were added to the water with agitation and mixed until homogeneous. At this point in Example 1, the ethylene oxide homopolymer was added with agitation and allowed to dissolve. The mixture was heated to about 48.89° C. (120° F.) and any pH adjusting agent, preservatives, dye solution and tetrasodium EDTA was added with agitation. Finally, when the composition was homogeneous, it was cooled to about 32.22° C. (90° F.) and the fragrance and any remaining salt or salt solution were added to the composition with agitation.

The ocular irritancy of each of the compositions was measured using the well-known Draize eye irritation testing method which is described in the Gilman et al. article noted above. For this testing, only three New Zealand white rabbits were used instead of the six normally employed in the Draize method and a 7 day observation period was used. The scores obtained for each composition are reported in Table II as well as a 7 day time weighted average score for each composition. The scores obtained after 24 hours, 48 hours, 72 hours and 7 days are the averages for the three rabbits tested for each shampoo composition tested.

The time weighted average score makes it easier to compare the ocular irritancy of each shampoo composition. As can be seen from Table II, Example 1 had the lowest time weighted average score of all of the compositions tested even though only 0.01% of the ethylene oxide homopolymer, POLYOX$^R$ WSRN-60-K, was employed. Example 2, which employed the sodium salts of sodium lauryl and laureth-3 sulfates instead of the ammonium salts used in Example 1, was much more irritating to the eyes as can be seen from a comparison of the seven day time weighted average and the 7 day score. Example 2 did contain more (11.75%) of the more irritating sodium lauryl sulfate than did Example 1 contain ammonium lauryl sulfate (7.35%) although the total amount of anionic surfactant present in each composition was comparable. Example 1 was comparable in ocular irritation to Example 5, but Example 5 employed an additional 1.6% of oleamidopropyl betaine while Example 1 only employed 0.01% of the ethylene oxide homopolymer. Example 1 had significantly lower ocular irritation scores than did the remaining shampoo compositions tested in this series.

EXAMPLES 8-11

These Examples further illustrate shampoo compositions prepared in accordance with the present invention. The shampoo compositions are given in Table III as well as the resulting pH and viscosity. It is believed that the ocular irritancy of these compositions will be similar to that obtained for Example 1. The viscosity of the shampoo compositions can be conventionally increased by adding more ammonium chloride solution. For example, the viscosity at 23.33° C. (74° F.) of Example 8 increased to 4,000 centipoise upon the addition of 1.8% more ammonium chloride solution.

EXAMPLES 1-7

TABLE I

| Example No.: | 1 | 2 | 3 | 4 | 5 | 6 | 7 |
|---|---|---|---|---|---|---|---|
| Ammonium Lauryl Sulfate (1) | (3) | — | 41.03 | 41.03 | 41.03 | — | 43.14 |
| Ammonium Laureth-1 Sulfate (13) | (3) | — | — | — | — | — | — |
| Ammonium Laureth-3 Sulfate (2) | — | — | 7.78 | 7.78 | 7.78 | — | 11.19 |
| Sodium Lauryl Sulfate (4) | — | 40.55 | — | — | — | — | — |
| Sodium Laureth-2 Sulfate | — | — | — | — | — | (11) | — |
| Sodium Laureth-3 Sulfate (5) | — | 10.89 | — | — | — | — | — |
| Ethylene Oxide Homoploymer (6) | 0.0117 | — | — | — | — | — | — |
| Oleamphopropyl Sulfonate (7) | — | — | 2.98 | — | — | — | — |
| Cocamidopropyl Hydroxysultaine (8) | — | — | — | 3.26 | — | — | — |
| Oleamidopropyl Betaine (9) | — | — | — | — | 5.45 | — | — |
| Cocamidopropyl Betaine | — | — | — | — | — | (11) | — |
| Lauric/Myristic DEA (10) | — | — | — | — | — | — | 2.00 |
| Ammonium Chloride (20% in water) | 5.0 | — | 2.35 | 3.00 | 2.40 | — | 1.00 |
| Ammonium Chloride (crystals) | — | 2.60 | — | — | — | — | — |
| Sodium Chloride (20% in water) | — | — | — | — | — | 3.00 | — |
| Citric Acid (50% in water) | — | — | 0.39 | 0.14 | 0.17 | — | 0.18 |
| Tetrasodium EDTA | — | — | 0.25 | 0.25 | 0.25 | — | 0.25 |
| Preservative Solution | — | — | 0.01 | 0.01 | 0.01 | — | 0.01 |
| Dye Solution | 2.0 | 2.00 | — | — | — | 0.30 | — |
| Fragrance | 0.5 | 0.5 | 0.50 | 0.50 | 0.5 | 0.5 | 0.50 |
| Deionized Water | 39.9883 | 43.46 | 44.71 | 44.03 | 42.41* | 68.61 | 41.73 |
| Totals | 100.0000 | 100.00 | 100.00 | 100.00 | 100.00 | 100.00 | 100.00 |
| pH | — | 4.64 | 5.61 | 5.39 | 5.15 | 7.52 | 5.78 |

TABLE I-continued

| Example No.: | 1 | 2 | 3 | 4 | 5 | 6 | 7 |
|---|---|---|---|---|---|---|---|
| Viscosity-centipoise (12) | 450 | 4900 | 4000 | 5600 | 3600 | 1400 | 3000 |

(1) SIPON® L22 from Alcolac, Ltd. with 29% actives level.
(2) SIPON® EA from Alcolac, Ltd. with 27% actives level.
(3) 52.5 parts of a 50:50 by weight of an aqueous blend of each surfactant having a combined actives level of 27% and containing 0.045% preservatives.
(4) SIPON® LSB from Alcolac, Ltd. with 29% actives level.
(5) SIPON® ES from Alcolac, Ltd. with 27% actives level.
(6) POLYOX® WSRN-60-K from Union Carbide Corporation which is PEG-45M of average molecular weight of about 2,000,000.
(7) SANDOTERIC® TFL Conc. from Sandoz Chemicals Corp. with 47% actives level.
(8) MIRATAINE® CBS from Miranol, Inc. with 43% actives level.
(9) CYCLOTERIC® BET 0-30 from Alcolac, Inc. with 30% actives level.
(10) CYCLOMIDE® DL207/S from Alcolac, Inc. with 100% actives which is a 1:1 blend of lauric diethanolamide:myristic diethanolamide.
(11) 27.59 parts of an aqueous blend containing, as actives, 49% sodium laureth-2-sulfate and 9% cocamidopropyl betaine.
(12) Brookfield Viscosimeter at 23.33° C. (74° F.) using #4 spindle at 30 r.p.m. for 30 seconds.
(13) SIPON® EAY from Alcolac, Ltd. with 26% actives level.

(5) SIPON$^R$ ES from Alcolac, Ltd. with 27% actives level. (6) POLYOX$^R$ WSRN-60-K from Union Carbide Corporation which is PEG-45M of average molecular weight of about 2,000,000. (7) SANDOTERIC$^R$ TFL Conc. from Sandoz Chemicals Corp. with 47% actives level. (8) MIRATAINE$^R$ CBS from Miranol, Inc. with 43% actives level. (9) CYCLOTERIC$^R$ BET 0-30 from Alcolac, Inc. with 30% actives level. (10) CYCLOMIDE$^R$ DL207/S from Alcolac, Inc. with 100% actives which is a 1:1 blend of lauric diethanolamide:myristic diethanolamide. (11) 27.59 parts of an aqueous blend containing, as actives, 49% sodium laureth-2-sulfate and 9% cocamidopropyl betaine. (12) Brookfield Viscosimeter at 23.33° C. (74° F.) using 4 spindle at 30 r.p.m. for 30 seconds. (13) SIPON$^R$ EAY from Alcolac, Ltd. with 26% actives level.

TABLE II

| Example No. | Observation | | | | 7 Day Time Weighted Avg. (1) |
|---|---|---|---|---|---|
| | 24 hrs. | 48 hrs. | 72 hrs. | 7 days | |
| 1 | 30.0 | 21.3 | 13.0 | 0.7 | 7.4 |
| 2 | 32.0 | 27.0 | 20.0 | 16.7 | 18.5 |
| 3 | 33.3 | 27.0 | 17.7 | 6.4 | 12.4 |
| 4 | 34.0 | 27.7 | 19.3 | 8.0 | 13.7 |
| 5 | 31.7 | 19.6 | 13.0 | 2.0 | 8.1 |
| 6 | 32.0 | 27.3 | 23.0 | 13.0 | 16.9 |
| 7 | 36.6 | 28.6 | 19.1 | 12.0 | 16.3 |

(1) The formula used is ((0.5 × 24 hr. reading) + 48 hr. reading +72 hr. reading + (4 × 7 day reading))/7

TABLE III

| Example No. | 8 | 9 | 10 | 11 |
|---|---|---|---|---|
| Deionized Water | 39.995 | 39.985 | 39.95 | 39.90 |
| Surfactant Blend (1) | 52.500 | 52.500 | 52.50 | 52.50 |
| POLYOX® WSRN-60-K | 0.005 | 0.015 | 0.05 | 0.10 |
| Dye Solution | 2.000 | 2.000 | 2.00 | 2.00 |
| Ammonium Chloride (20% in water) | 5.000 | 5.000 | 5.00 | 5.00 |
| Fragrance | 0.500 | 0.500 | 0.50 | 0.50 |
| Totals | 100.000 | 100.000 | 100.00 | 100.00 |
| pH | 3.79 | 3.65 | 3.63 | 3.69 |
| Viscosity-centipoise | 1000 | 800 | 700 | 700 |

(1) a 50:50 by weight of an aqueous blend of ammonium lauryl sulfate and ammonium laureth-1 sulfate having a combined actives level of 27%.
(2) Brookfield Viscosimeter at 23.33° C. (74° F.) using #4 spindle at 30 r.p.m. for 30 seconds.

What is claimed is:

1. A method of reducing the ocular irritancy of an aqueous shampoo composition consisting essentially of from about 1 to about 20% by weight of at least one eye irritating anionic surfactant selected from the group consisting of $C_8$–$C_{18}$ alkyl sulfates containing from 0 to an average of about 4 ethyleneoxy units per molecule, $C_8$–$C_{18}$ alkyl benzene sulfonates, $C_8$–$C_{25}$ olefin sulfonates, $C_{10}$–$C_{20}$ paraffin sulfonates, $C_8$–$C_9$ alkyl phenol ethoxamer sulfates and mixtures thereof and the balance consisting essentially of water, said method comprising including within said shampoo composition from about 0.005% to about 5% by weight of an ethylene oxide homopolymer of the formula $H(OCH_2CH_2)_xOH$ as the sole additive to reduce the ocular irritation of the shampoo, the value of x being such that the weight average molecular weight of the homopolymer is from about 100,000 to about 5,000,000.

2. The method as claimed in claim 1 wherein the value of x is such that the molecular weight of the homopolymer is from about 500,000 to about 4,000,000 and the amount is from about 0.01 to 1% by weight of the shampoo composition.

3. The method as claimed in claim 2 wherein the sole anionic surfactant present is selected from $C_8$–$C_{18}$ alkyl sulfates containing from 0 to an average of about 4 ethyleneoxy units per molecule.

4. The method as claimed in claim 3 wherein the anionic surfactant is selected from $C_{12}$ alkyl sulfates containing from 0 to an average of about 4 ethyleneoxy units per molecule.

5. The method as claimed in claim 3 wherein the anoinic surfactant is an ammonium or sodium salt of $C_{12}$ alkyl sulfates containing from 0 to an average of about 4 ethyleneoxy units per molecule.

6. The method as claimed in claim 3 wherein the homopolymer is from 0.01 to 0.5% by weight.

7. The method as claimed in claim 4 wherein the ethylene oxide homopolymer has a number average molecular weight of about 2,000,000.

* * * * *